United States Patent [19]

Horodysky

[11] Patent Number: 4,618,436

[45] Date of Patent: Oct. 21, 1986

[54] MULTIFUNCTIONAL LUBRICANT ADDITIVES AND COMPOSITIONS THEREOF

[75] Inventor: Andrew G. Horodysky, Cherry Hill, N.J.

[73] Assignee: Mobil Oil Corporation, New York, N.Y.

[21] Appl. No.: 750,197

[22] Filed: Jul. 1, 1985

[51] Int. Cl.⁴ ............... C10M 129/00; C10M 137/00; C10M 139/00

[52] U.S. Cl. .................. 252/325; 252/49.6; 252/49.9; 548/110

[58] Field of Search .................. 252/49.9, 32.5, 49.6; 548/110

[56] References Cited

U.S. PATENT DOCUMENTS

| | | | |
|---|---|---|---|
| 3,030,375 | 4/1962 | DeGray | 548/110 |
| 4,116,876 | 9/1978 | Brois et al. | 252/49.6 |
| 4,162,224 | 7/1979 | Bridger | 252/49.6 |
| 4,557,844 | 12/1985 | Horodysky | 252/49.6 |

Primary Examiner—William R. Dixon, Jr.
Assistant Examiner—Cynthia A. Prezlock
Attorney, Agent, or Firm—Alexander J. McKillop; Michael G. Gilman; Howard M. Flournoy

[57] ABSTRACT

Borated internal oxazoline acid phosphates provide effective antiwear and friction reducing characteristics for lubricant compositions when incorporated therein.

27 Claims, No Drawings

MULTIFUNCTIONAL LUBRICANT ADDITIVES AND COMPOSITIONS THEREOF

BACKGROUND OF THE INVENTION

This invention is directed to lubricant compositions containing small additive concentrations of reaction products which possess excellent multifunctional high temperature stabilizing, antiwear and friction modifying activity. This invention is also directed to such additives as novel compositions of matter.

The need for antiwear, friction reducing modifiers, and high temperature stability in lubricating oils to meet the ever changing requirements of modern equipment is well known. Various materials and various techniques have been proposed.

The use of oxazolines is known for their surfactant and lubricity properties when formulated into lubricating oils and for their water scavenging and dispersant characteristics when blended into fuels.

The use of phosphorus containing lubricating additives has also found widespread use. Phosphonates have been found to be lubricity and antiwear agents as exemplified by U.S. Pat. No. 4,356,097 which describes the use of dihydrocarbyl phosphonates in lubricant formulations.

U.S. Pat. No. 3,920,567 describes quaternary salts formed as the reaction product of an alkyl phosphonate and a hydroxyalkyl oxazoline as useful antiwear and extreme pressure agents in lubricating oils.

The use of boron containing compounds has been extensively reported in such diverse applications as hydraulic fluids and brake fluids, as well as in fuel compositions.

SUMMARY OF THE INVENTION

In accordance with the present invention, it has now been found that the use of novel zwitterionic (internal) acid phosphate salts of borated oxazolines provides lubricants with highly effective friction reducing properties and high temperature stabilizing activity. Furthermore these unique borated internal oxazoline-derived acid phosphates not only provide greater antiwear activity than traditional acid oxazolines but have greater potential friction reducing activity than previously reported with prior art acid phosphates. The exceptional surface activity of these novel additives, coupled with the oxazoline moiety, apparently provide the basis for the significant synergistic friction-reducing activity for a variety of synthetic and mineral oil based lubricants, greases and liquid hydrocarbyl fuels.

DESCRIPTION OF THE PREFERRED EMBODIMENTS

The oxazolines in accordance with the present invention have the following generalized structure:

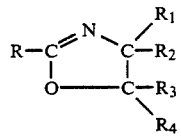

Wherein R is from about $C_8$ to about $C_{30}$ hydrocarbyl or

such as an acyl sarcosine-derived substituent or mixtures thereof, at least one of $R_1$, $R_2$, $R_3$ or $R_4$ is hydroxyalkyl having from 1 to about 6 carbon atoms and the remaining $R_1$, $R_2$, $R_3$ and $R_4$ are independently selected from the group consisting of $C_1$ to about $C_{30}$ hydrocarbyl, $C_1$ to about $C_6$ hydroxyalkyl, hydrogen or

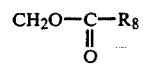

where $R_8$ is hydrogen or $C_1$ to about $C_{30}$ hydrocarbyl, or

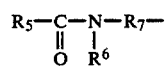

or mixtures thereof, $R_5$ is about $C_8$ to about $C_{30}$ hydrocarbyl $R_6$ is $C_1$ to about $C_6$ hydrocarbyl, and $R_7$ is $C_1$ to about $C_3$ hydrocarbylene.

The above hydroxyalkyl hydrocarbyl oxazolines are converted to their corresponding acid phosphates by reaction with molar quantities, more than molar quantities, or less than molar quantities of phosphorus pentoxide. This can be from about 5 to 100% wt. molar quantities of $P_2O_5$ to form a product containing from about 0.01% to 10% wt. phosphorus, or more preferably from about 0.1% to about 5% wt. phosphorus. Preferably the reaction takes place with up to molar quantities of $P_2O_5$ at temperatures of from about 50° to 110° C. wherein the $P_2O_5$ is added incrementally as the reactor temperature is increased. The reaction can take up to approximately 10–12 hours or more. Although depending upon the reactants and reaction parameters, the reaction may be completed in less than about 10 hours.

A mixture of products is believed to form during the reaction with phosphorus pentoxide; at least a portion of which contains the zwitterionic (internal) oxazoline acid phosphate salt having the below generalized structure:

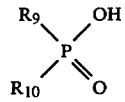

wherein at least one of $R_9$ and $R_{10}$ has an oxazoline moiety as described above and the other $R_9$ or $R_{10}$ is hydroxyl or $C_2$ to about $C_8$ hydrocarbyl. The reaction mixture is thereafter borated by any convenient means such as by reaction with boric acid, trialkyl borates, metaborates, boron oxide or any other similar means as described below. Convenient borating agents may be summarized as follows: $(R_{11}O)_xB(OH)_y$ where $R_{11}$ is $C_1$ to about $C_{16}$ hydrocarbyl, x is 0 to 3 and y is 0 to 3 with the proviso that x+y must equal 3. Boration can be accomplished using less than stoichiometric or more than stoichiometric quantities of boron to produce a product containing from about 0.01% to about 10% boron and more preferably 0.19% to 5% boron.

A preferred hydrocarbyl oxazoline is prepared by the reaction of oleic acid and stearic acid with tris(hydroxymethyl) aminomethane. However, the oxazolines in accordance herewith may be obtained commercially or by any process or reaction known to the art. With the use of molar quantities of reagents dihydroxyalkyl oxazolines are formed. With the use of 2 moles of acid hydroxyalkyl oxazoline esters are formed. Either of these oxazolines or mixtures thereof can be used in the present invention.

The described zwitterionic oxazoline-derived borated acid phosphates may be further reacted with an amine to yield a corresponding borated oxazoline-derived internal acid phosphate amine. Any suitable hydrocarbyl amine may be used. The borated hydroxyalkyl hydrocarbyl (or sarcosyl) oxazoline additives may be prepared by the following generalized reaction:

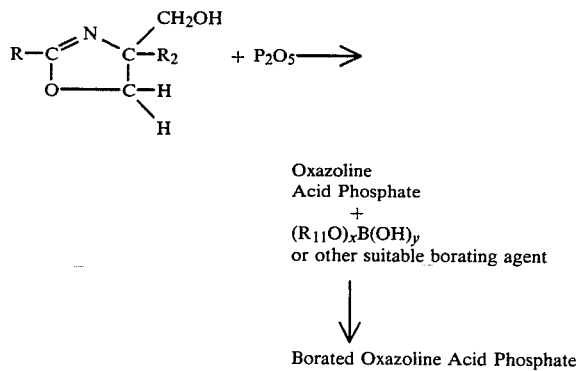

Oxazoline Acid Phosphate
+
$(R_{11}O)_xB(OH)_y$
or other suitable borating agent

↓

Borated Oxazoline Acid Phosphate $R_2$, $R_{11}$, x and y are as defined herein above. A preferred acyl sarcosine-derived oxazoline can be prepared by the reaction of oleyl sarcosine with tris (hydroxymethyl) aminomethane. Said sarcosines can also include lauroyl, cocoyl, tallowyl, soyoyl, stearoyl, isostearoyl, decanoyl sarcosines and similar sarcosines or mixtures of sarcosines. Mixtures of sarcosines and fatty acids can be used to prepare said oxazolines. Oxazolines derived from sarcosines or mixtures thereof are often preferred.

Included among the suitable amines, but not limited thereto, are monoalkylamines such as methyl amine, t-alkyl primary amines, oleylamine, tallowamine, dialkylamines such as dioctylamine, dioleylamine, oleylmethylamine, aryl amines such as 4-ethylaniline or phenyl- or naphthylamine, and heterocyclic amines such as imidazolines and diamines such as N-oleyl-1,3-propylenediamine, etheramines such as tetradecyl or propylene amino etherdiamines.

The additives embodied herein are utilized in lubricating oil or grease compositions in an amount which imparts significant antiwear characteristics to the oil or grease as well as reducing the friction of the engine operating with the oil in its crankcase. Concentrations of about 0.001 to about 10 wt. % based on the total weight of the composition can be used. Preferably, the concentration is from about 0.1 to about 3 wt. %.

The additives have the ability to improve the antiwear characteristics and friction reducing characteristics of various oleaginous materials such as hydrocarbyl lubricating media which may comprise liquid oils in the form of either a mineral oil or a synthetic oil, or in the form of a grease in which the aforementioned oils are employed as a vehicle.

In general, mineral oils, both paraffinic, naphthenic and mixtures thereof, employed as the lubricant, or grease vehicle, may be of any suitable lubricating viscosity range, as for example, from about 45 SSU at 100° F. to about 6000 SSU at 100° F., and preferably, from about 50 to about 250 SSU at 210° F. These oils may have viscosity indexes ranging to about 100 or higher. Viscosity indexes from about 70 to about 95 are preferred. The average molecular weights of these oils may range from about 250 to about 800. Where the lubricant is to be employed in the form of a grease, the lubricating oil is generally employed in an amount sufficient to balance the total grease composition, after accounting for the desired quantity of the thickening agent, and other additive components to be included in the grease formulation.

A wide variety of materials may be employed as thickening or gelling agents. These may include any of the conventional metal salts or soaps, such as calcium stearates, lithium hydroxystearates or the like, which are dispersed in the lubricating vehicle in grease-forming quantities in an amount to impart to the resulting grease composition the desired consistency. Other thickening agents that may be employed in the grease formulation may comprise the non-soap thickeners, such as surface-modified clays and silicas, aryl ureas, calcium complexes and similar materials. In general, grease thickeners may be employed which do not melt and dissolve when used at the required temperature within a particular environment; however, in all other respects, any materials which is normally employed for thickening or gelling hydrocarbon fluids for forming grease can be used in preparing grease in accordance with the present invention.

In instances where synthetic oils, or synthetic oils employed as the vehicle for the grease, are desired in preference to mineral oils, or in combination therewith, various compounds of this type may be successfully utilized. Typical synthetic vehicles include, but are not limited to, polyisobutylene, polybutenes, hydrogenated polydecenes, polypropylene glycol, polyethylene glycol, trimethylolpropane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated synthetic oils, chain-type polyphenyls, siloxanes and silicones (polysiloxanes), alkyl-substituted diphenyl ethers typified by a butyl-substituted bis (p-phenoxy phenyl) ether, phenoxy phenylethers.

It is to be understood, however, that the compositions contemplated herein can also contain other materials. For example, corrosion inhibitors, extreme pressure agents, viscosity index improvers, co-antioxidants, other antiwear agents and the like can be used as exemplified by calcium or magnesium, metallic borates or sulfonates, polymeric succinimides, metallic (zinc) phosphorodithioates and the like. These materials do not detract from the value of the compositions of this invention, rather the materials serve to impart their customary properties to the particular compositions in which they are incorporated.

The following examples illustrate the invention. They are illustrative only and are not meant to limit it.

EXAMPLE 1

Part A

Approximately 175 g of an acyl sarcosine-derived oxazoline, prepared by the reaction of molar amounts of oleyl sarcosine and tris(hydroxymethyl) aminomethane until dehydration was complete at about 170° C., and 100 ml n-hexane were placed into a reactor and warmed to about 60° C. under N₂ blanket. Approximately 125 g phosphorus pentoxide was added incrementally over two hours at 60°-70° C. The reactants were then held at about 110° C. for two hours and about 130° C. for two hours. Approximately 175 g diluent oil (100 second solvent paraffinic neutral lubricating oil) was added to reduce viscosity and improve handling. The solvent was removed by vacuum distillation at 130° C. and the diluted product was filtered through diatomaceous earth.

Part B.

Approximately 100 g of the above product of Part A, 100 g toluene, and 10 g boric acid were heated to 150° C. over a period of about six hours in a reactor equipped with heater, agitator, Dean-Stark tube with condenser, until water evolution during azeotropic distillation ceased (approximately 7 g water was collected). The solvent was removed by vacuum distillation at about 150° C. and the borated product was filtered through diatomaceous earth.

EXAMPLE 2

Part A.

Approximately 175 g of the acyl sarcosine-derived oxazoline described in Example 1, 100 ml n-hexane, and 25 g phosphorus pentoxide were reacted as generally described in Example 1, Part A. The reactants were then held at about 100° C. for two hours, about 130° C. for two hours and 175 g diluent oil (100 second SPN lubricating oil) was added. The solvent was removed by vacuum distillation at 130° C. and the diluted product was filtered through diatomaceous earth.

Part B.

Approximately 100 g of the above product of Part A, 100 g toluene and 10 g boric acid were reacted at up to 150° C., as generally described in Example 1, Part B, until water evolution during azeotropic distillation ceased (approximately 6 g water was collected). The solvent was removed by vacuum distillation at about 150° C. and the borated product was filtered through diatomaceous earth.

The products were blended into fully formulated oils and evaluated for their friction reducing properties as shown in Tables 1 and 2.

The borated products of the examples were blended into mineral oil at 1% concentration and evaluated in the Shell Four-Ball Wear Test using a 60 kg load at 1500 RPM for thirty minutes as shown in Table 1 and tested for friction modifying characteristics in the Low Velocity Friction Apparatus (LVFA) in fully formulated mineral or synthetic automotive engine oils containing antioxidant, dispersant and detergent additives.

Evaluation of the Reaction Products

In the Shell Four-Ball Wear Test, three stationary balls are placed in the lubricant cup and the lubricant containing the compound to be tested is added thereto, and a fourth ball is placed in a chuck mounted on a device which can be used to spin the ball at known speeds and loads. The samples were tested using ½ inch stainless steel balls of 52100 steel for 30 minutes.

The LVFA is fully described in Mobil U.S. Pat. No. 4,511,482.

The data disclosed in the Tables clearly demonstrate the antiwear and friction modifying effectiveness of the compositions which contain the borated internal acid phosphate salts described herein. They are useful at low concentrations, are ashless and do not contain any potentially undesirable sulfur or metallic salts. They may be readily prepared in a two-step one-pot process, comparable in many respects to known reactions currently practiced commercially.

TABLE 1

Four-Ball Wear Test Results

| | Concentration in Base Oil, Wt. % | Scar-Diameter, MM (60 kg load, 1500 RPM, 30 Minutes) | |
|---|---|---|---|
| | | 175° F. | 275° F. |
| Base Oil (fully formulated mineral oil) | — | 2.0 | 2.2 |
| Example 2 | 1.0 | 1.5 | 1.7 |

The results clearly demonstrate the antiwear effectiveness of the compositions.

TABLE 2

Frictional Characteristics

| | Additive Concentration Wt. % | Reduction or % Change in Coefficient of Friction | |
|---|---|---|---|
| | | 5 Ft/Min | 30 Ft/Min |
| Base Oil A (fully formulated synthetic engine oil containing detergent/dispersant/inhibitor performance package) SAE 10W/30 | — | 0 | 0 |
| Example 1 - Borated oleoyl sarcosine-derived oxazoline acid phosphate | 2.0 | 41 | 36 |
| | 1.0 | 36 | 24 |
| Example 2 - Borated oleoyl sarcosine-derived oxazoline acid phosphate | 2.0 | 17 | 12 |

The results clearly show the friction-reducing properties of the compositions.

TABLE 3

Frictional Characteristics

| | Additive Concentration Wt. % | Reduction or % Change in Coefficient of Friction | |
|---|---|---|---|
| | | 5 Ft/Min | 30 Ft/Min |
| Base Oil B (fully formulated mineral oil derived engine oil containing detergent/dispersant/inhibitor performance package) SAE 10W/40 | — | 0 | 0 |
| Example 1 - Borated oleoyl sarcosine-derived oxazoline acid phosphate | 2.0 | 15 | — |
| | 1.0 | 36 | 24 |

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. A composition comprising a major proportion of an oil of lubricating viscosity or grease prepared therefrom and a minor antiwear or friction reducing proportion of a borated oxazoline derived internal acid phosphate prepared by reacting a hydroxyalkyl hydrocarbyl oxazoline having the following generalized structure with phosphorus pentoxide

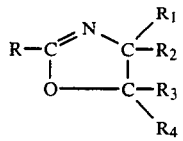

wherein R is from about $C_8$ to about $C_{30}$ hydrocarbyl or

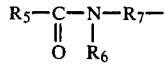

or mixtures thereof and at least one of $R_1$, $R_2$, $R_3$ or $R_4$ is hydroxyalkyl having from 1 to about 6 carbon atoms and the remaining $R_1$, $R_2$, $R_3$ and $R_4$ are independently selected from the group consisting of $C_1$ to about $C_{30}$ hydrocarbyl, $C_1$ to about $C_6$ hydroxyalkyl, hydrogen or

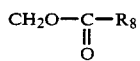

where $R_8$ is hydrogen or $C_1$ to about $C_{30}$ hydrocarbyl, or

or mixtures thereof and wherein $R_5$ is from about $C_8$ to about $C_{30}$ hydrocarbyl, $R_6$ is from about $C_1$ to about $C_6$ hydrocarbyl and $R_7$ is from about $C_1$ to about $C_3$ hydrocarbylene, obtaining the corresponding oxazoline-derived internal acid phosphate having the generalized structure

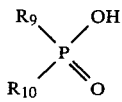

wherein at least one of $R_9$ and $R_{10}$ has an oxazoline moiety as described herein and the other $R_9$ or $R_{10}$ is hydroxyl or $C_2$ to about $C_8$ hydrocarbyl, and thereafter borating said oxazoline acid phosphate with a suitable borating agent.

2. The composition of claim 1 wherein the borating agent is selected from the group consisting essentially of $(R_{11}O)_xB(OH)_y$, boron oxides and metaborates wherein $R_{11}$ is from $C_1$ to about $C_{16}$ hydrocarbyl, x is 0 to 3 and y is 0 to 3 with the proviso x+y must equal 3.

3. The composition of claim 2 wherein the borating agent is boric acid.

4. The composition of claim 1 wherein R is

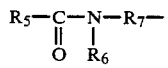

or mixtures thereof and wherein said substituent is derived from an acyl sarcosine.

5. The composition of claim 4 wherein said acyl sarcosine is selected from the group consisting essentially of oleoyl, lauroyl, cocoyl, decanoyl, isostearoyl, stearoyl, soyoyl and tallowoyl sarcosines.

6. The composition of claim 5 wherein said hydroxyalkyl hydrocarbyl oxazoline is prepared by the reaction of oleyl sarcosine with tris (hydroxymethyl) aminomethane.

7. The composition of claim 1 wherein the reaction is carried out at temperatures of from about 50 to about 110° C. with substantially molar quantities of phosphorous pentoxide.

8. The composition of claim 7 wherein the reaction is carried out over a period of about ten hours or less.

9. The composition of claim 1 wherein said major proportion is selected from the group consisting of mineral oils, synthetic oils, mixtures thereof or greases prepared therefrom.

10. The composition of claim 9 wherein said major proportion is a mineral oil.

11. The composition of claim 9 wherein said major proportion is a synthetic oil.

12. The composition of claim 9 wherein said major proportion is a grease.

13. The composition of claim 1 wherein the borated oxazoline derived acid phosphate is further reacted with a hydrocarbyl amine.

14. An additive product consisting of an oxazoline derived internal acid phosphate prepared by reacting a hydroxyalkyl hydrocarbyl oxazoline having the following generalized structure with phosphorus pentoxide:

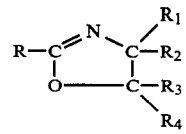

wherein R is from about $C_8$ to about $C_{30}$ hydrocarbyl or

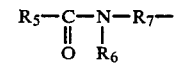

or mixtures thereof at least one of $R_1$, $R_2$, $R_3$ and $R_4$ is hydroxyalkyl having from 1 to about 6 carbon atoms and the remaining $R_1$, $R_2$, $R_3$ and $R_4$ are independently selected from the group consisting of $C_1$ to about $C_{30}$ hydrocarbyl, $C_1$ to about $C_6$ hydroxyalkyl, hydrogen or

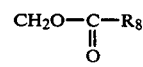

where $R_8$ is hydrogen or $C_1$ to about $C_{30}$ hydrocarbyl, or

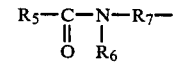

or mixtures thereof and $R_5$ is from $C_8$ to about $C_{30}$ hydrocarbyl, $R_6$ is $C_1$ to about $C_6$ hydrocarbyl and $R_7$ is $C_1$ to about $C_3$ hydrocarbylene to produce an internal acid phosphate having the following generalized structure

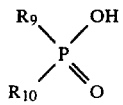

wherein at least one of $R_9$ and $R_{10}$ has an oxazoline moiety as described herein and the other $R_9$ or $R_{10}$ is hydroxyl or $C_2$ to about $C_8$ hydrocarbyl and thereafter borating said acid phosphate.

15. The additive product of claim 14 wherein the reaction is carried out at temperatures of from about 50 to about 110° C. with substantially molar quantities of phosphorous pentoxide.

16. The additive product of claim 15 wherein the borated additive product described therein is further reacted with a hydrocarbyl amine to obtain the corresponding borated oxazoline derived acid phosphate amine.

17. The additive product of claim 16 wherein the borating means or agent is selected from the group consisting essentially of $(R_{11}O)_3B(OH)_3$, boron oxides and metaborates wherein $R_{11}$ is from $C_1$ to about $C_{16}$ hydrocarbyl, x is 0 to 3 and y is 0 to 3 with the proviso that x+y must equal 3.

18. The additive product of claim 17 wherein the borating agent is boric acid.

19. The additive product of claim 14 wherein R is

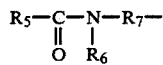

or mixtures thereof and wherein said substituent is derived from an acyl sarcosine.

20. The additive product of claim 19 wherein said acyl sarcosine is selected from the group consisting essentially of oleoyl, lauroyl, cocoyl, decanoyl, isostearoyl, stearoyl, soyoyl and tallowoyl sarcosines.

21. The composition of claim 14 wherein said hydroxyalkyl hydrocarbyl oxazoline is prepared by the reaction of oleyl sarcosine with tris (hydroxymethyl) aminomethane.

22. An additive product prepared by the following generalized reaction:

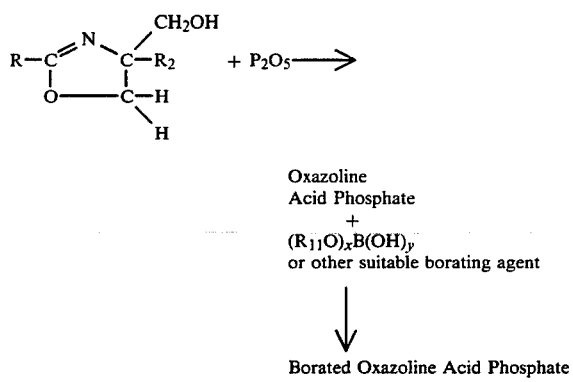

wherein
R and $R_2$ are selected from the group consisting essentially of oleoyl, lauroyl, cocoyl, decanoyl, isostearoyl, stearoyl, soyoyl and tallowoyl sarcosines;
and wherein $R_{11}$ is $C_1$ to about $C_{16}$ hydrocarbyl; x is 0 to 3, y is 0 to 3 with the proviso that x+y must equal 3.

23. The additive product prepared as in claim 22 wherein R contains a sarcosine derived substituent.

24. An additive prepared as in claim 22 which is further reacted with a hydrocarbyl amine or substituted hydrocarbyl amine to produce the corresponding borated oxazoline derived acid phosphate amine.

25. The product of claim 22 wherein R is an acyl sarcosine substituent derived from the group consisting essentially of oleoyl, lauroyl, cocoyl, decanoyl, isostearoyl, stearoyl, soyoyl and tallowoyl sarcosines.

26. The product of claim 22 wherein the hydroxyalkyl hydrocarbyl oxazoline is prepared from oleoyl sarcosine and tris (hydroxymethane) aminomethane.

27. A method of reducing fuel consumption comprising treating the moving parts of an internal combustion engine with a composition as described in claim 1.

* * * * *